United States Patent
Vardanyan et al.

(10) Patent No.: US 10,766,925 B2
(45) Date of Patent: Sep. 8, 2020

(54) OPIOID RECEPTOR MODULATORS

(71) Applicant: Arizona Board of Regents on behalf of the University of Arizona, Tucson, AZ (US)

(72) Inventors: Ruben Vardanyan, Tucson, AZ (US); Victor Hruby, Tucson, AZ (US)

(73) Assignee: Arizona Board of Regents on behalf of the University of Arizona, Tucson, AZ (US)

( * ) Notice: Subject to any disclaimer, the term of this patent is extended or adjusted under 35 U.S.C. 154(b) by 0 days.

(21) Appl. No.: 16/090,102

(22) PCT Filed: Apr. 11, 2017

(86) PCT No.: PCT/US2017/027063
§ 371 (c)(1),
(2) Date: Sep. 28, 2018

(87) PCT Pub. No.: WO2017/180659
PCT Pub. Date: Oct. 19, 2017

(65) Prior Publication Data
US 2019/0112333 A1    Apr. 18, 2019

Related U.S. Application Data

(60) Provisional application No. 62/321,155, filed on Apr. 11, 2016, provisional application No. 62/321,152, filed on Apr. 11, 2016.

(51) Int. Cl.
| | | |
|---|---|---|
| C07D 211/58 | (2006.01) | |
| C07K 4/00 | (2006.01) | |
| A61K 38/00 | (2006.01) | |

(52) U.S. Cl.
CPC .............. *C07K 4/00* (2013.01); *C07D 211/58* (2013.01); *A61K 38/00* (2013.01)

(58) Field of Classification Search
CPC .............................. C07D 211/58; A61K 38/00
See application file for complete search history.

(56) References Cited

U.S. PATENT DOCUMENTS 9,765,027 B2 *   9/2017  Vardanyan ........... C07D 211/58

FOREIGN PATENT DOCUMENTS

| WO | 2003082819 | * | 10/2003 |
| WO | 2005030722 | * | 4/2005 |

OTHER PUBLICATIONS

Florkiewicz, Acta Anaestesiologica Scandinavica, vol. 59, 999-1008, 2015. (Year: 2015).*
Gomez-Brouchet, J Transl Med, vol. 13(208), 1-3, 2015. (Year: 2015).*
Lee, J Med Chem, vol. 54, 382-386, 2011. (Year: 2011).*

* cited by examiner

*Primary Examiner* — D Margaret M Seaman
(74) *Attorney, Agent, or Firm* — Don D. Cha; HDC IP Law, LLP

(57) ABSTRACT

The present invention provides compounds that can modulate opioid receptors. Some compounds of the invention are modulators of μ- and/or δ-opioid receptors. Still other compounds of the invention are opioid receptor antagonists. Some compounds of the invention can modulate opioid receptors with a significantly less likelihood of developing addiction or abuse compared to conventional opioid ligands, such as morphine. In particular, compounds of the invention are of the formula:

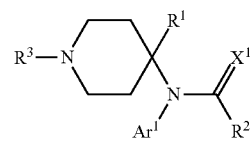

I wherein
$Ar^1$ is H, optionally substituted aryl or optionally substituted heteroaryl;
$R^1$ is a heteroalkyl;
$R^2$ is alkyl;
$R^3$ is an oligopeptide or a moiety of the formula $-R^4-Y$;
$R^4$ is alkylene;
Y is optionally substituted heteroaryl, optionally substituted aryl or a moiety of the formula $-C(=X^2)-X^3-R^5$;
each of $X^1$, $X^2$ and $X^3$ is independently O, $NR^6$ or S; and
each of $R^5$ and $R^6$ is independently H or alkyl.

20 Claims, No Drawings

OPIOID RECEPTOR MODULATORS

CROSS-REFERENCE TO RELATED APPLICATIONS

This application claims the priority benefit of U.S. Provisional Application Nos. 62/321,152, filed Apr. 11, 2016, and 62/321,155, filed Apr. 11, 2016, all of which are incorporated herein by reference in their entirety.

STATEMENT REGARDING FEDERALLY FUNDED RESEARCH

This invention was made with government support under Grant Nos. R01 DA006284 and R01 DA013449 awarded by the National Institutes of Health. The government has certain rights in the invention.

FIELD OF THE INVENTION

The present invention relates to compounds that can modulate opioid receptors or selective modulators of μ- and/or δ-opioid receptors. Some compounds of the invention can modulate opioid receptors with a significantly less likelihood of developing addiction or abuse compared to conventional opioid ligands, such as morphine. In particular, some compounds of the invention are selective μ-opioid receptor agonists and/or δ-opioid receptor agonists while other compounds of the invention are opioid receptor antagonists.

BACKGROUND OF THE INVENTION

Opioid analgesics have been used for centuries and remain to this day the most potent and reliable analgesic agents. They are used routinely and effectively for the treatment of acute and chronic pain. Currently, approximately 90% of patients with chronic pain receive opioids. Opioids not only provide potent analgesia but also reduce anxiety and produce mild sedation and a palpable sense of well-being, often to the point of euphoria.

Unfortunately, prolonged administration of opioid analgesics causes physical dependence and addiction. Physical dependence is a state of physiological adaption manifested by a withdrawal syndrome produced by abrupt discontinuation of a medication. Addiction is a chronic neurobiological disease resulting in the use of a drug for non-therapeutic purposes. Addiction is progressive and can result in disability or premature death.

There are other problems associated with the chronic use of opioid analgesics including, but not limited to, the development of antinociceptive tolerance. Tolerance is a state of adaptation in which exposure to a drug induces changes that result in diminution of its effects over time. Tolerance of the drug require use of higher doses over time to elicit the same level of analgesia.

High doses of opioids result in serious side effects such as impairment of mental alertness, sedation, somnolence, dizziness, nausea, vomiting, urinary retention, constipation, pruritus and others. Unfortunately, use of opioids for pain treatment has now been transformed to a social problem similar to problems associated with methamphetamine, cocaine or other illegal drugs.

Opioid abuse is an epidemic all over the world. It is believed that the number of new opioid abusers had increased by 225% between 1992 and 2000. In fact, in 2010 there were as many as 2.4 million opioid abusers in the United States alone. The U.S. Centers for Disease Control and Prevention (CDC) reported that drug-overdose deaths reached a new high in 2014, totaling 47,055 people in which 60% was due to opioids.

Opioid receptor antagonists (i.e., "opioid antagonists") are drugs that bind to the opioid receptors, typically with higher affinity than agonists. Unlike agonists, antagonists do not activate the receptors to which they bind. Thus, opioid antagonists are often used to block the receptor from the action of agonists to counteract life-threatening depression of the central nervous and respiratory systems. Accordingly, opioid antagonists are often used to treat opioid overdose and opioid dependency.

Opioid receptor antagonists modulate or attenuate numerous central and peripheral effects including opioid abuse, the development of tolerance and dependence, and opioid-induced constipation, alcohol and cocaine abuse, depression, and immune responses. The diverse therapeutic applications of μ-opioid receptor antagonists include opioid-overdose-induced respiratory depression, opioid and cocaine abuse, alcohol dependence, smoking cessation, obesity, psychosis and for therapies for dyskinesia associated with Parkinson's disease.

Commonly known opioid antagonists include naltrexone, naloxone and nalmefene which have therapeutic utility in a variety of conditions. Opioid antagonists effectively block the receptor from the action of both naturally occurring agonists (e.g., morphine, codeine, thebaine) and synthetic agonists (e.g., fentanyl, pethidine, levorphanol, methadone, tramadol, dextropropoxyphene) and uses include counteracting life-threatening depression of the central nervous and respiratory systems.

During the last two decades only Alvimopan, a peripherally acting μ-opioid receptor antagonist for the treatment of postoperative ileus has been approved as new drug, and some azabicyclohexane derivatives and series of bi(hetero) aryl ethers as biological tools have been proposed as new chemical entities in this class of compounds.

In a commonly assigned PCT Patent Application No. PCT/US15/46585 and the corresponding U.S. patent application Ser. No. 14/834,185, both of which were filed on Aug. 24, 2015, and are incorporated herein by reference in their entirety, treatment of various clinical conditions using substituted 1-arylalkyl-4-acylaminopiperidine compounds are discussed, such as those associated with opioid abuse, the development of opioid tolerance and dependence, opioid-induced constipation, cocaine abuse, depression, and immune responses, opioid-overdose-induced respiratory depression, alcohol dependence, smoking cessation, obesity, psychosis, dyskinesia associated with Parkinson's disease, Raynaud's disease, hypertension, scleroderma, anxiety and panic disorders.

Despite the various opioid antagonists that are currently available, there is a continuing need for other opioid antagonists. In addition, there is a need for a compound that provides potent analgesia without causing undesired side-effects including addiction and dependency.

SUMMARY OF THE INVENTION

Some aspects of the invention are based on the discovery by the present inventors that practically every chemical class of compounds with opioid-agonist activity has a structurally similar opioid-antagonist pair. In one particular aspect of the invention, the present inventors have discovered that transformation of opioid agonist to opioid antagonist can be achieved by a structural change in the existing agonist.

Still other aspects of the invention provide compounds that are μ-opioid receptor modulators ("μ-opioid modulators") and/or δ-opioid receptor modulators ("δ-opioid modulators"). In some embodiments, compounds of the invention are μ-opioid receptor agonists ("μ-opioid agonists") and/or δ-opioid receptor agonists.

Opioids are generally defined by their actions at one of the family of opioid G-protein coupled receptors μ-, δ-, κ- and the nociception receptor. However, it has been shown that only agonists at μ-opioid receptors consistently produce potent analgesia. Several studies indicate that δ-opioid receptor agonists as well as δ-opioid receptor antagonists can provide beneficial modulation to the pharmacological effects of μ-opioid receptor agonists. For example, it has been shown that δ-opioid receptor agonists can enhance the analgesic potency and efficacy of μ-opioid receptor agonists. It has also been shown that δ-opioid receptor antagonists can prevent or diminish the development of addiction, tolerance and physical dependence that may result from μ-opioid receptor agonists. Accordingly, δ-opioid receptor agonists can be used to increase the analgesic potency and efficacy of morphine or other opioids, whereas δ-opioid receptor antagonists can be used to prevent or reduce addiction, tolerance or dependency of opioids.

One particular aspect of the invention provides a compound of the formula:

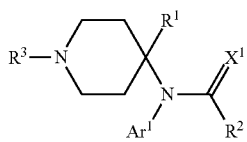

where $Ar^1$ is H, optionally substituted aryl or optionally substituted heteroaryl; $R^1$ is a heteroalkyl; $R^2$ is alkyl; $R^3$ is an oligopeptide or a moiety of the formula —$R^4$—Y; $R^4$ is alkylene; Y is optionally substituted heteroaryl, optionally substituted aryl or a moiety of the formula —C(=$X^2$)—$X^3$—$R^5$; each of $X^1$, $X^2$ and $X^3$ is independently O, $NR^6$ or S; and each of $R^5$ and $R^6$ is independently H or alkyl. Depending on the particular substituents in compounds of Formula I, compounds of Formula I can be μ-opioid modulators, δ-opioid modulators, or both, or they can be opioid receptor antagonists.

In some embodiments, μ-opioid modulators and/or δ-opioid modulators are those of Formula I, where $Ar^1$ is optionally substituted aryl or optionally substituted heteroaryl; $R^1$ is a heteroalkyl; $R^2$ is alkyl; $R^3$ is an oligopeptide; and $X^1$ is O, $NR^6$ or S; and $R^6$ is H or alkyl.

Yet in other embodiments, compounds of Formula I are opioid antagonists when $Ar^1$ is H or optionally substituted heteroaryl; $R^1$ is a heteroalkyl; $R^2$ is alkyl; $R^3$ is an oligopeptide or a moiety of the formula —$R^4$—Y, where $R^4$ is alkylene; and Y is optionally substituted heteroaryl, optionally substituted aryl or a moiety of the formula —C(=$X^2$)—$X^3$—$R^5$, where $X^2$ and $X^3$ is independently O, $NR^6$ or S; and each of $R^5$ and $R^6$ is independently H or alkyl.

DETAILED DESCRIPTION OF THE INVENTION

"Alkyl" refers to a saturated linear monovalent hydrocarbon moiety of one to twelve, typically one to six, carbon atoms or a saturated branched monovalent hydrocarbon moiety of three to twelve, typically three to six, carbon atoms. Exemplary alkyl group include, but are not limited to, methyl, ethyl, n-propyl, 2-propyl, tert-butyl, pentyl, and the like.

"Alkylene" refers to a saturated linear saturated divalent hydrocarbon moiety of one to twelve, typically one to six, carbon atoms or a branched saturated divalent hydrocarbon moiety of three to twelve, typically three to six, carbon atoms. Exemplary alkylene groups include, but are not limited to, methylene, ethylene, propylene, butylene, pentylene, and the like.

"Aryl" refers to a monovalent mono-, bi- or tricyclic aromatic hydrocarbon moiety of 6 to 15 ring atoms which is optionally substituted with one or more substituents within the ring structure. When substituted, aryl group typically has one, two, or three substituents within the ring structure. When two or more substituents are present in an aryl group, each substituent is independently selected. Exemplary substituents for the aryl group include alkyl, haloalkyl, thioalkyl, heteroalkyl, halo, nitro, cyano, optionally substituted phenyl, heteroaryl, heterocyclyl, haloalkoxy, —COR (where R is alkyl or haloalkyl), -(alkylene)$_n$-COOR (where n is 0 or 1 and R is hydrogen, alkyl, or haloalkyl), or -(alkylene)$_n$-CONR$^a$R$^b$ (where n is 0 or 1, and R$^a$ and R$^b$ are, independently of each other, hydrogen, or alkyl). More specifically the term aryl includes, but is not limited to, phenyl, 1-naphthyl, and 2-naphthyl, each of which can be optionally substituted.

The term "heteroaryl" means a monovalent monocyclic or bicyclic aromatic moiety of 5 to 12 ring atoms containing one, two, or three ring heteroatoms selected from N, O, or S, the remaining ring atoms being C. The heteroaryl ring is optionally substituted independently with one or more substituents, typically selected from alkyl, haloalkyl, heteroalkyl, heterocyclyl, halo, nitro, cyano, carboxy, acyl, -(alkylene)$_n$-COOR (where n is 0 or 1 and R is hydrogen, alkyl, optionally substituted phenylalkyl, or optionally substituted heteroaralkyl), or -(alkylene)$_n$-CONR$^a$R$^b$ (where n is 0 or 1, and R$^a$ and R$^b$ are, independently of each other, hydrogen, alkyl, cycloalkyl, cycloalkylalkyl, hydroxyalkyl, aryl, or R$^a$ and R$^b$ together with the nitrogen atom to which they are attached form a heterocyclyl ring). More specifically the term heteroaryl includes, but is not limited to, pyridyl, furanyl, thiophenyl, thiazolyl, isothiazolyl, triazolyl, imidazolyl, isoxazolyl, pyrrolyl, pyrazolyl, pyrazinyl, pyrimidinyl, benzofuranyl, isobenzofuranyl, benzothiazolyl, benzoisothiazolyl, benzotriazolyl, indolyl, isoindolyl, benzoxazolyl, quinolyl, isoquinolyl, benzimidazolyl, benzisoxazolyl, benzothiophenyl, dibenzofuran, and benzodiazepin-2-one-5-yl, and the like.

"Aralkyl" refers to a moiety of the formula —R$^b$R$^c$ where R$^b$ is an alkylene group and R$^c$ is an aryl group as defined herein. Exemplary aralkyl groups include, but are not limited to, benzyl, phenylethyl, 2-(4-chlorophenyl)ethyl, 2-(4-fluorophenyl)ethyl, and the like.

"Chiral center" (i.e., stereochemical center, stereocenter, or stereogenic center) refers to an asymmetrically substituted atom, e.g., a carbon atom to which four different groups are attached. The ultimate criterion of a chiral center, however, is nonsuperimposability of its mirror image.

"Cycloalkyl" refers to a non-aromatic, typically saturated, monovalent mono- or bicyclic hydrocarbon moiety of three to ten ring carbons. The cycloalkyl can be optionally substituted with one or more substituents within the ring structure. When two or more substituents are present in a cycloalkyl group, each substituent is independently selected. Exemplary substituents for cycloalkyl group include alkyl, haloalkyl, halo, cyano, heteroalkyl, etc. More specifically, the term cycloalkyl includes, for example, cyclopropyl, cyclohexyl, cyclopentyl, and the like.

"Cycloalkylalkyl" refers to a moiety of the formula —$R^dR^e$ where $R^d$ is an alkylene group and $R^e$ is a cycloalkyl group as defined herein. Exemplary cycloalkylalkyl groups include, but are not limited to, cyclopropylmethyl, cyclohexylpropyl, 3-cyclohexyl-2-methylpropyl, and the like.

The terms "halo," "halogen" and "halide" are used interchangeably herein and refer to fluoro, chloro, bromo, or iodo.

"Haloalkyl" refers to an alkyl group as defined herein in which one or more hydrogen atom is replaced by same or different halo atoms. The term "haloalkyl" also includes perhalogenated alkyl groups in which all alkyl hydrogen atoms are replaced by halogen atoms. Exemplary haloalkyl groups include, but are not limited to, —$CH_2Cl$, —$CF_3$, —$CH_2CF_3$, —$CH_2CCl_3$, and the like.

"Heteroalkyl" refers to an alkyl group as defined herein in which one or more carbon atom in the chain is replaced with a heteroatom (e.g., O, N, S(O)n, where n is 0, 1 or 2) and/or where one or more carbon atom in the chain is substituted with a carbonyl or carboxyl group (e.g., a moiety of the formula —COX, where X is H, alkyl, —OR, —$NR^aR^b$, —$SR^c$, etc., where each of $R^a$, $R^b$ and $R^c$ is independently H or alkyl). Exemplary heteroalkyl includes, but is not limited to, 2-methoxyethyl, methoxymethyl, 2-hydroxyethyl, —$(CH_2)_2CO_2CH_3$, —$CO_2CH_3$, and the like.

"Heterocyclyl" means a non-aromatic monocyclic moiety of three to eight ring atoms in which one or two ring atoms are heteroatoms selected from N, O, or $S(O)_n$ (where n is an integer from 0 to 2), the remaining ring atoms being C, where one or two C atoms can optionally be a carbonyl group. The heterocyclyl ring can be optionally substituted independently with one or more substituents. When two or more substituents are present in a heterocyclyl group, each substituent is independently selected. Exemplary substituents for heterocyclyl group include, but are not limited to, alkyl, haloalkyl, heteroalkyl and halo. Exemplary heterocyclo includes, but is not limited to, tetrahydropyranyl, piperidino, piperazino, morpholino and thiomorpholino, thiomorpholino-1-oxide, thiomorpholino-1,1-dioxide, and the like.

"Oligopeptide" refers to two or more linked amino acids. Typically, oligopeptide has two to ten, more typically two to eight, often two to six and more often three to five, and most often three or four linked amino acids. The term "amino acid" includes naturally occurring amino acids as well as synthetic amino acids. In general, the term "amino acid" refers to a compound of the formula $HO_2CCR^{a1}R^{a2}NH_2$, where each of $R^{a1}$ and $R^{a2}$ is independently H, alkyl, haloalkyl, aralkyl, heteroaralkyl, heteroalkyl, etc. each of which may be optionally substituted.

"Enantiomeric excess" refers to the difference between the amount of enantiomers. The percentage of enantiomeric excess (% ee) can be calculated by subtracting the percentage of one enantiomer from the percentage of the other enantiomer. For example, if the % ee of (R)-enantiomer is 99% and % ee of (S)-enantiomer is 1%, the % ee of (R)-isomer is 99%-1% or 98%.

"Leaving group" has the meaning conventionally associated with it in synthetic organic chemistry, i.e., an atom or a group capable of being displaced by a nucleophile and includes halo (such as chloro, bromo, and iodo), alkanesulfonyloxy, arenesulfonyloxy, alkylcarbonyloxy (e.g., acetoxy), arylcarbonyloxy, mesyloxy, tosyloxy, trifluoromethanesulfonyloxy, aryloxy (e.g., 2,4-dinitrophenoxy), methoxy, N,O-dimethylhydroxylamino, and the like.

"Pharmaceutically acceptable excipient" refers to an excipient that is useful in preparing a pharmaceutical composition that is generally safe, non-toxic and neither biologically nor otherwise undesirable, and includes excipient that is acceptable for veterinary use as well as human pharmaceutical use.

"Pharmaceutically acceptable salt" of a compound means a salt that is pharmaceutically acceptable and that possesses the desired pharmacological activity of the parent compound. Such salts include: (1) acid addition salts, formed with inorganic acids such as hydrochloric acid, hydrobromic acid, sulfuric acid, nitric acid, phosphoric acid, and the like; or formed with organic acids such as acetic acid, propionic acid, hexanoic acid, cyclopentanepropionic acid, glycolic acid, pyruvic acid, lactic acid, malonic acid, succinic acid, malic acid, maleic acid, fumaric acid, tartaric acid, citric acid, benzoic acid, 3-(4-hydroxybenzoyl)benzoic acid, cinnamic acid, mandelic acid, methanesulfonic acid, ethanesulfonic acid, 1,2-ethane-disulfonic acid, 2-hydroxyethanesulfonic acid, benzenesulfonic acid, 4-chlorobenzenesulfonic acid, 2-naphthalenesulfonic acid, 4-toluenesulfonic acid, camphorsulfonic acid, 4-methylbicyclo[2.2.2]-oct-2-ene-1carboxylic acid, glucoheptonic acid, 3-phenylpropionic acid, trimethylacetic acid, tertiary butylacetic acid, lauryl sulfuric acid, gluconic acid, glutamic acid, hydroxynaphthoic acid, salicylic acid, stearic acid, muconic acid, and the like; or (2) salts formed when an acidic proton present in the parent compound either is replaced by a metal ion, e.g., an alkali metal ion, an alkaline earth ion, or an aluminum ion; or coordinates with an organic base such as ethanolamine, diethanolamine, triethanolamine, tromethamine, N-methylglucamine, and the like.

The term "modulate" in reference to affecting activity of a receptor means that the compound can act as either an agonist or an antagonist.

The terms "pro-drug" and "prodrug" are used interchangeably herein and refer to any compound which releases an active parent drug according to Formula I in vivo when such prodrug is administered to a mammalian subject. Prodrugs of a compound of Formula I are prepared by modifying one or more functional group(s) present in the compound of Formula I in such a way that the modification(s) may be cleaved in vivo to release the parent compound. Prodrugs include compounds of Formula I wherein a hydroxy, amino, or sulfhydryl group in a compound of Formula I is bonded to any group that may be cleaved in vivo to regenerate the free hydroxyl, amino, or sulfhydryl group, respectively. Examples of prodrugs include, but are not limited to, esters (e.g., acetate, formate, and benzoate derivatives), carbamates (e.g., N,N-dimethylaminocarbonyl) of hydroxy functional groups in compounds of Formula I, and the like.

"Protecting group" refers to a moiety, except alkyl groups, that when attached to a reactive group in a molecule masks, reduces or prevents that reactivity. Examples of protecting groups can be found in T. W. Greene and P. G. M. Wuts, *Protective Groups in Organic Synthesis*, 3$^{rd}$ edition, John Wiley & Sons, New York, 1999, and Harrison and Harrison et al., *Compendium of Synthetic Organic Methods*, Vols. 1-8 (John Wiley and Sons, 1971-1996), which are incorporated herein by reference in their entirety. Representative hydroxy protecting groups include acyl groups, benzyl and trityl ethers, tetrahydropyranyl ethers, trialkylsilyl ethers and allyl ethers. Representative amino protecting groups include, formyl, acetyl, trifluoroacetyl, benzyl, benzyloxycarbonyl (CBZ), tert-butoxycarbonyl (Boc), trimethyl silyl (TMS), 2-trimethylsilyl-ethanesulfonyl (SES), trityl and substituted trityl groups, allyloxycarbonyl, 9-fluorenylmethyloxycarbonyl (FMOC), nitro-veratryloxycarbonyl (NVOC), and the like.

"Corresponding protecting group" means an appropriate protecting group corresponding to the heteroatom (i.e., N, O, P or S) to which it is attached.

"A therapeutically effective amount" means the amount of a compound that, when administered to a mammal for treating a disease, is sufficient to effect such treatment for the disease. The "therapeutically effective amount" will vary depending on the compound, the disease and its severity and the age, weight, etc., of the mammal to be treated.

"Treating" or "treatment" of a disease includes: (1) preventing the disease, i.e., causing the clinical symptoms of the disease not to develop in a mammal that may be exposed to or predisposed to the disease but does not yet experience or display symptoms of the disease; (2) inhibiting the disease, i.e., arresting or reducing the development of the disease or its clinical symptoms; or (3) relieving the disease, i.e., causing regression of the disease or its clinical symptoms.

As used herein, the term "treating", "contacting" or "reacting" refers to adding or mixing two or more reagents under appropriate conditions to produce the indicated and/or the desired product. It should be appreciated that the reaction which produces the indicated and/or the desired product may not necessarily result directly from the combination of two reagents which were initially added, i.e., there may be one or more intermediates which are produced in the mixture which ultimately leads to the formation of the indicated and/or the desired product.

As used herein, the terms "those defined above" and "those defined herein" when referring to a variable incorporates by reference the broad definition of the variable as well as preferred, more preferred and most preferred definitions, if any.

Compounds of the Invention: Some aspects of the invention provide a compound of the formula:

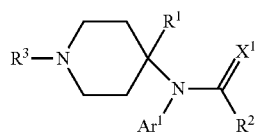

I where $Ar^1$ is H, optionally substituted aryl or optionally substituted heteroaryl; $R^1$ is a heteroalkyl; $R^2$ is alkyl; $R^3$ is an oligopeptide or a moiety of the formula —$R^4$—Y; $R^4$ is alkylene; Y is optionally substituted heteroaryl, optionally substituted aryl or a moiety of the formula —C(=$X^2$)—$X^3$—$R^5$; each of $X^1$, $X^2$ and $X^3$ is independently O, $NR^6$ or S; and each of $R^5$ and $R^6$ is independently H or alkyl. Depending on the particular substituents in compounds of Formula I, compounds of Formula I can be μ-opioid modulators, δ-opioid modulators, or both, or they can be opioid receptor antagonists.

Opioid Antagonists: Opioid antagonists are drugs that bind to the opioid receptors, typically with higher affinity than agonists. Opioid antagonists generally do not activate the receptors, but displaces or blocks opioid agonist from binding to the receptors. Opioid antagonists can be used to counteract life-threatening depression of the central nervous and respiratory systems, and therefore are often used for emergency overdose and dependence treatment. Because opioid receptor antagonists modulate numerous central and peripheral effects, they can be used to treat, for example, (i) opioid-overdose-induced respiratory depression; (ii) opioid abuse, addiction and development of tolerance and dependence; (iii) alcohol and cocaine abuse and addiction; (iv) nicotine addiction; (v) gambling addiction; (vi) neuropathic pain; (vii) depression; (viii) levodopa-induced dyskinesia on Parkinson's disease; (ix) opioid-induced constipation and other functional gastrointestinal disorders as well as many other clinical conditions. In addition, opioid receptor antagonists can be used in rapid detoxification and for maintenance therapy in opioid withdrawal.

Opioid antagonists currently marketed in USA (Naloxone, Naltrexone and Nalmefene) are considered universal opioid receptor antagonists. They are competitive opioid receptor antagonists at μ-, κ- and δ-opioid receptors with preference for μ-receptors. Studies have shown these opioid antagonists can displace opioids that are bound to α-receptors. These known opioid antagonists can rapidly reverse the effects of morphine and other opioid agonists and have two primary clinical uses: the treatment of opioid overdose and the prevention and treatment of opioid dependence and addiction. These compounds show no noticeable action on normal persons, but have shown to reverse poisoning and withdrawal symptoms in opioid addicts.

Some aspects of the invention are based on the discovery by the present inventors that practically every chemical class of compounds with opioid-agonist activity has a structurally similar opioid-antagonist pair. Further study by the present inventors have led to the discovery that agonist-antagonist transformation typically takes place as a result of the some, often small, structural change in the existing agonist.

Some compounds of Formula I are opioid antagonists. In some embodiments, opioid antagonists are compound of Formula I where $Ar^1$ is H or optionally substituted heteroaryl; $R^1$ is a heteroalkyl; $R^2$ is alkyl; $R^3$ is an oligopeptide or a moiety of the formula —$R^4$—Y, where $R^4$ is alkylene; and Y is optionally substituted heteroaryl, optionally substituted aryl or a moiety of the formula —C(=$X^2$)—$X^3$—$R^5$, where each of $X^2$ and $X^3$ is independently O, $NR^6$ or S; and each of $R^5$ and $R^6$ is independently H or alkyl.

In some embodiments, $Ar^1$ is optionally substituted heteroaryl. In one particular embodiment, $Ar^1$ is optionally substituted pyridyl or optionally substituted pyrazinyl. Exemplary $Ar^1$ groups include, but are not limited to, optionally substituted pyrid-2-yl (i.e., a moiety of the formula A) and optionally substituted pyrazinyl (i.e., a moiety of the formula B):

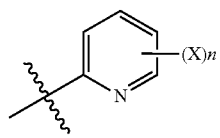

A

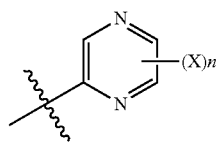

B where for a moiety of Formula A: n is an integer of 0-4; and X is a substituent as defined herein; and for a moiety of Formula B: n is an integer of 0-3; and X is a substituent as defined herein. In one particular embodiment, $Ar^1$ is pyrazin-2-yl (i.e., n is 0). In another embodiment, for a moiety of Formula A: n is 1 and X is alkyl, often methyl. In some embodiments, the methyl substituent is on the 5-position of the pyridyl ring.

Still in another embodiment, $R^1$ is a heteroalkyl of the formula: —C(=O)—$OR^7$ or —$R^8$—$X^4$—$R^9$, where each of $R^7$ and $R^9$ is independently H or alkyl; $R^8$ is alkylene; $X^4$ is O, $NR^{10}$ or S; and $R^{10}$ is H, alkyl or a nitrogen protecting group. Within this embodiment, in some instances, $R^1$ is a heteroalkyl of the formula: —C(=O)—$OR^7$. In some cases, $R^7$ is alkyl. In one particular case, $R^7$ is methyl. Still in another instance, $R^1$ is a heteroalkyl of the formula: —$R^8$—$X^4$—$R^9$, wherein $R^8$, $X^4$ and $R^9$ are those defined herein. In one particular case, $R^8$ is methylene. Still in another case, $X^4$ is O. Yet in another case, $R^9$ is alkyl. In one particular case, $R^9$ is methyl.

In other embodiments, $R^3$ is a moiety of the formula: —$R^4$—Y, where $R^4$ and Y are those defined herein. In some embodiments, $R^4$ is ethylene. Yet in other embodiments, Y is selected from the group consisting of optionally substituted 5-oxo-4,5-dihydro-1H-tetrazol-1-yl, optionally substituted thiophen-2-yl, optionally substituted phenyl and a moiety of the formula —C(=O)—$OR^5$, where $R^5$ is as defined herein. Some of the specific opioid antagonist compounds of the invention include, but are not limited to, the following compounds:

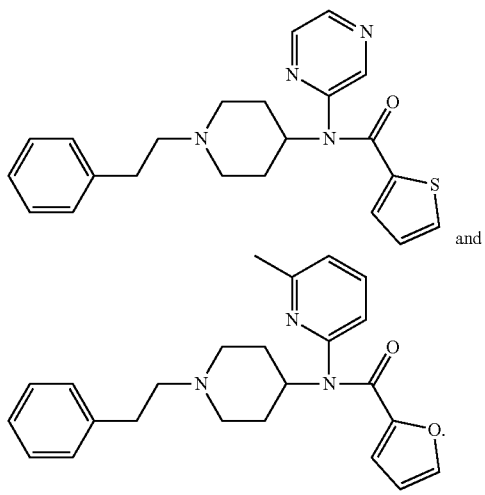

and

Other representative compounds of the invention include, but are not limited to, the following compounds:

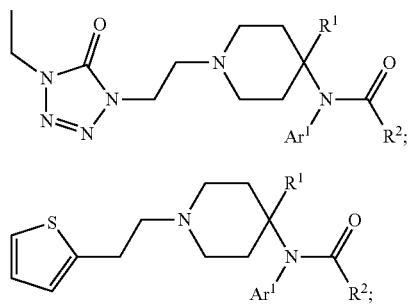

I-A

I-B

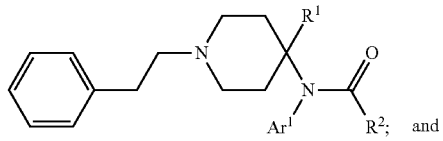

I-C and

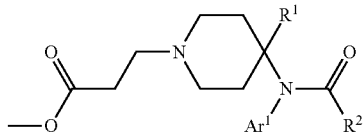

I-D where $R^1$, $R^2$ and $Ar^1$ are those defined herein. In some embodiments, $R^2$ is alkyl, such as $C_1$-$C_4$ alkyl, typically ethyl. In another embodiment, for compounds of Formulas I-A and I-B, $R^1$ is a heteroalkyl moiety of the formula —$CH_2OCH_3$. Still in other embodiments, for compounds of Formulas I-C and I-D, $R^1$ is a heteroalkyl moiety of the formula —$CO_2CH_3$.

Selective μ- and/or δ-Opioid Modulators: Currently no opioid ligands exist that retain high analgesic potency but with reduced abuse or addiction potential. This lack of progress in development of drugs with powerful analgesia without the addictive potential is one of the main impediments to treating chronic pain and other clinical conditions associated with using opioid receptor agonists.

Opioid antagonists can be used not only for treatment of various addictions induced by both prescription medications and street drugs but also for the treatment of alcohol or nicotine abuse, for treatment of cancer, control of dyskinesia-induced by levodopa during Parkinson's disease, for treatment of obesity as well as other various clinical.

Some aspects of the invention provide compounds that can be used to treat pain and other clinical conditions associated with using opioid receptor ligands, such as morphine, but with reduced or without the abusive and/or addictive properties. Some compounds of the invention modulate μ-opioid receptor, δ-opioid receptor, or both. In some embodiments, compounds of the invention possess μ-agonist and δ-agonist activity. In another embodiment, compounds of the invention possess μ-agonist and δ-antagonist activity. As discussed above, μ- and δ-opioid receptor ligands modulate one another's function in vivo allowing to avoid or reduce the centrally-mediated side effects and abuse potential.

In one particular embodiment, the invention provides a compound of the formula:

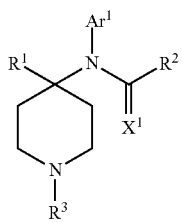

I where $Ar^1$ is optionally substituted aryl or optionally substituted heteroaryl; $R^1$ is a heteroalkyl; $R^2$ is alkyl; $R^3$ is an oligopeptide; $X^1$ is O, $NR^4$ or S; and $R^4$ is H or alkyl.

In some embodiments, $Ar^1$ is optionally substituted aryl. In other embodiments, $Ar^1$ is optionally substituted phenyl. In one particular embodiment, $Ar^1$ is phenyl.

Yet in other embodiments, $R^1$ is a heteroalkyl of the formula:

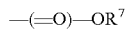 II or

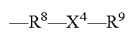 III where each of $R^7$ and $R^9$ is independently H or alkyl; $R^8$ is alkylene; $X^4$ is O, $NR^{10}$ or S; and $R^{10}$ is H, alkyl or a nitrogen protecting group. Within these embodiments, in some instances $R^1$ is a heteroalkyl of the formula: —C(=O)—$OR^7$, where $R^7$ is as defined herein. Typically, $R^7$ is alkyl. In one specific embodiment, $R^7$ is methyl. Still in another instances of these embodiments, $R^1$ is a heteroalkyl of the formula: —$R^8$—$X^4$—$R^9$, where $R^8$, $X^4$ and $R^9$ are those defined herein. In one particular instance, $R^8$ is methylene. In another instance $X^4$ is O. Yet in another instance, $R^9$ is alkyl, typically $C_{1-6}$ alkyl. In one specific case, $R^9$ is methyl.

Still in another embodiment, $R^3$ is an oligopeptide having two to five and typically three or four amino acids. In one particular embodiment, the oligopeptide (i.e., $R^3$) is a moiety of the formula:

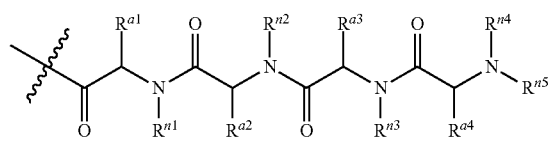 IV where each of $R^{a1}$, $R^{a2}$, $R^{a3}$ and $R^{a4}$ is independently amino acid side-chain; and each of $R^{n1}$, $R^{n2}$, $R^{n3}$, $R^{n4}$ and $R^{n5}$ is independently H, alkyl or a nitrogen protecting group.

The amino acid side-chains are well known to one skilled in the art. Exemplary amino acid side-chains include those of naturally occurring amino acid side-chains such as —$CH_3$ (Alanine), —$(CH_2)_3NHC(=NH)NH_2$ (Arginine), —$CH_2C(=O)NH_2$ (Asparagine), —$CH_2CO_2H$ (Aspartic acid), —$CH_2SH$ (Cysteine), —$CH_2CH_2C(=O)NH_2$ (Glutamine), —$(CH_2)_2CO_2H$ (Glutamic acid), —H (Glysine), —CH(Et)$CH_3$ (Isoleucine),

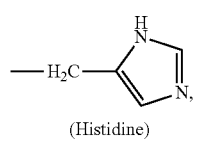 , 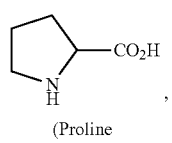

(Histidine) (Proline it should be noted that in proline, the amino acid side-chain (e.g., $R^{a1}$) and the "R" group of the nitrogen (e.g., $R^{n1}$) together with the carbon atom and the nitrogen atom to which $R^{a1}$ and $R^{n1}$ are attached to form the five-membered heterocyclyl ring, i.e., pyrrolidine moiety), —$(CH_2)_4NH_2$ (Lysine), —$CH_2CH_2SCH_3$ (Methionine), —$CH_2CH(CH_3)_2$ (Leucine), —$CH_2Ph$ (Phenylalanine), —$CH_2OH$ (Serine), —$CH(OH)CH_3$ (Threonine),

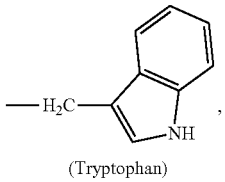 , 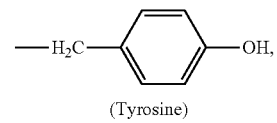

(Tryptophan) (Tyrosine)

and —$CH(CH_3)_2$ (Valine), as well as derivatives thereof, such as those in which the phenyl ring of phenylalanine is substituted with one or more substituents such as halide, alkyl, hydroxyl, alkoxy (e.g., —OR', where R' is alkyl), amino, cyano, haloalkyl, etc. Some of the specific representative amino acid side-chains that are useful in compounds of the invention include, but are not limited to, those described above, but more specifically —H, —$(CH_2)_nCH_3$ (where n an integer from 0-6, typically 0, 1, 2 or 3, often 0, 2 or 3), —$CH_2$—Ar (where Ar is phenyl, 4-halosubstituted phenyl, 2,5-dialkyl-4-hydroxyphenyl, 4-hydroxyphenyl, etc.

In one particular embodiment, each of the amino acid side-chain of moiety of Formula IV is independently selected from the group consisting of H, alkyl and —$R^{11}$—$Ar^2$, wherein $R^{11}$ is alkylene and $Ar^2$ is optionally substituted aryl. Within this embodiment, in some instances, $R^{11}$ is methylene, ethylene or propylene, often methylene. Still in other instances, each $Ar^2$ is independently selected from the group consisting of halo-substituted phenyl and dialkyl-hydroxy substituted phenyl.

Yet in another embodiment, moiety of Formula IV is of the formula:

IV-A

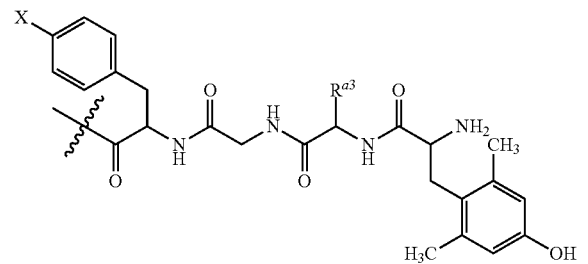

where X is halide; and $R^{a3}$ is alkyl. In some instances, X is chloro or fluoro. Still in other instances, $R^{a3}$ is methyl or butyl.

Still in another embodiment, $R^3$ is -(4-halo, e.g., Cl or F)Phe-$A^1$-$A^2$-(2,5-dimethyl)Tyr, where each of $A^1$ and $A^2$ is independently an amino acid. Yet in another embodiment, $R^3$ is -Phe-Gln-D-Arg-Leu-(4-Cl)Phe-Gly-D-Ala-Dmt-$NH_2$, where "D" refers to (D)-isomer of an amino acid and Dmt is N,N-Dimethyltryptamine.

Synthesis: It should be noted combinations of the various groups described herein form other embodiments. In this manner, a variety of preferred compounds are embodied within the present invention. It should also be appreciated that unless otherwise explicitly stated each of the amino acid can be independently (L)- or (D)-isomer.

Compounds of the invention can be synthesized using various techniques and synthetic procedures known to one skilled in the art. For example, a synthesis of related compounds shown below have been described by Bagley et al., in "New 4-(heteroanilido) piperidines, structurally related to the pure opioid agonist fentanyl, with agonist and/or antagonist properties," *J. Med. Chem.*, 1989, 32(3), 663-671; France et al., in "Pharmacological profile of a novel fentanyl derivative with opioid and nonopioid effects," *J. Pharm. and Exp. Therap.*, 1991, 258(2), 502-510; Egan et al., in "Mirfentanil and A-4334. Tritiation at high specific activity," *Applied Radiation and Isotopes*, 2009, Volume Date 2010, 68(1), 120-121; Aceto et al., M. D.; Bowman, E. R.; Harris, L. S.; Hughes, Larry D.; Kipps et al., in "Dependence studies of new compounds in the rhesus monkey, rat and mouse (2002)," From NIDA Research Monograph (2003), 183 (Problems of Drug Dependence 2002), 191-227; Gerak et al. in "Effects of a Novel Fentanyl Derivative on Drug Discrimination and Learning in Rhesus Monkeys," *Pharmacology, Biochemistry and Behavior*, 1999, 64(2), 367-371; Petrov et al., in "Synthesis and evaluation of 3-aminopropionyl substituted fentanyl analogues for opioid activity," *Bioorganic & Medicinal Chemistry Letters*, 2006, 16(18), 4946-4950 and Petrov et al. in "Effect of anchoring 4-anilinopiperidines to opioid peptides," *Bioorganic & Medicinal Chemistry Letters*, 2013, 23(11), 3434-3437, all of which are incorporated herein by reference in their entirety. In particular, the latter two references describes synthesis of the following amino acid substituted opioid analogs.

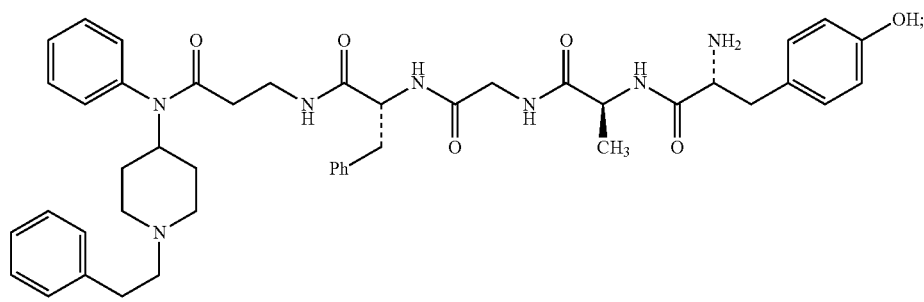

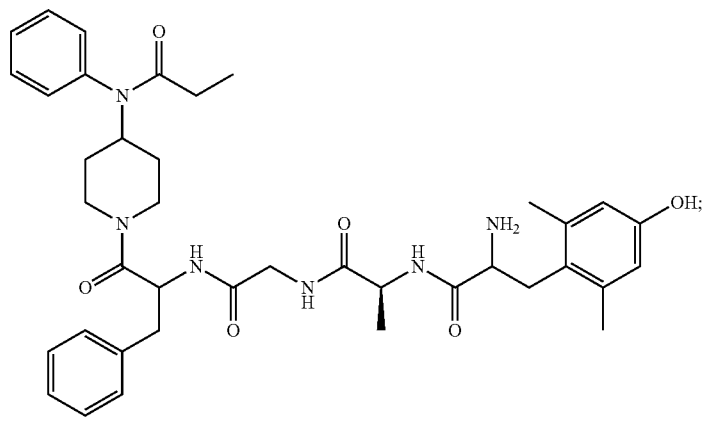

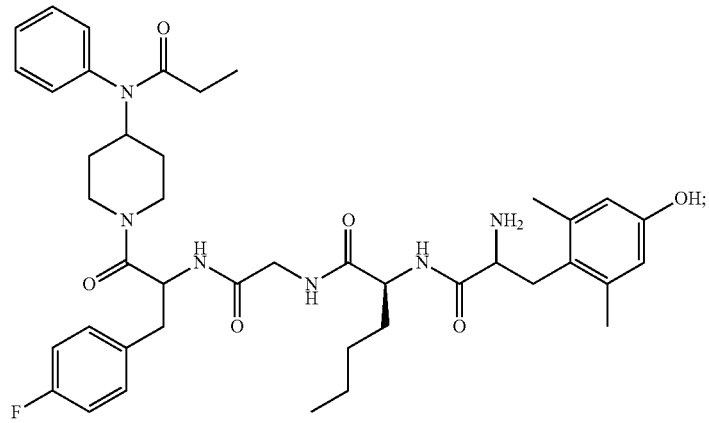

-continued

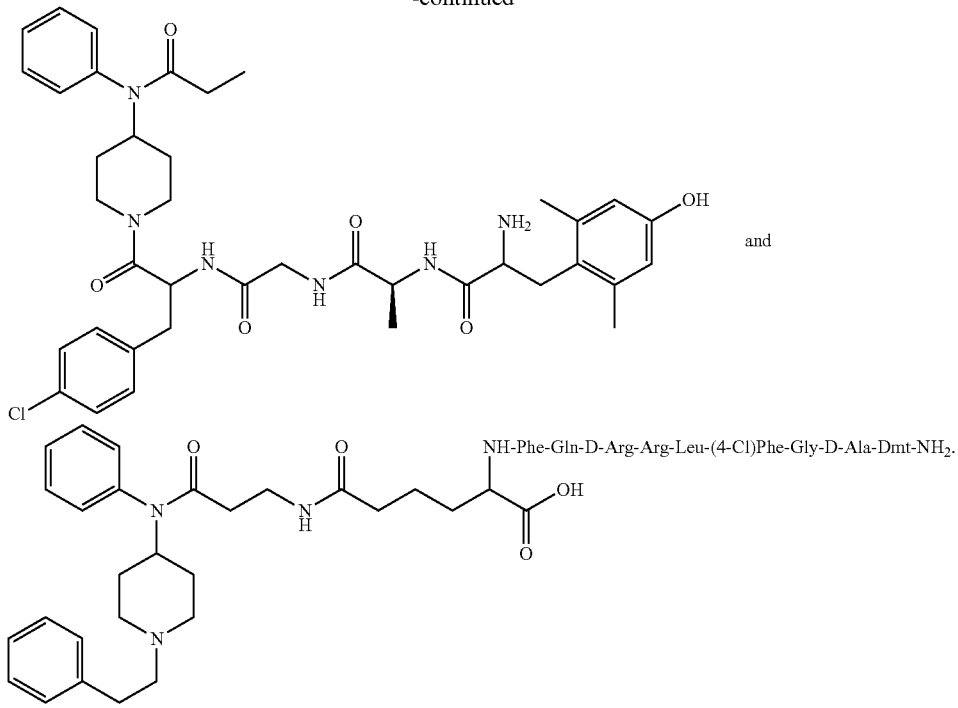

NH-Phe-Gln-D-Arg-Arg-Leu-(4-Cl)Phe-Gly-D-Ala-Dmt-NH$_2$.

One can utilize a similar strategy and chemistry to produce the compounds of the invention. Some of the specific representative compounds of the invention include, but are not limited to the following compounds:

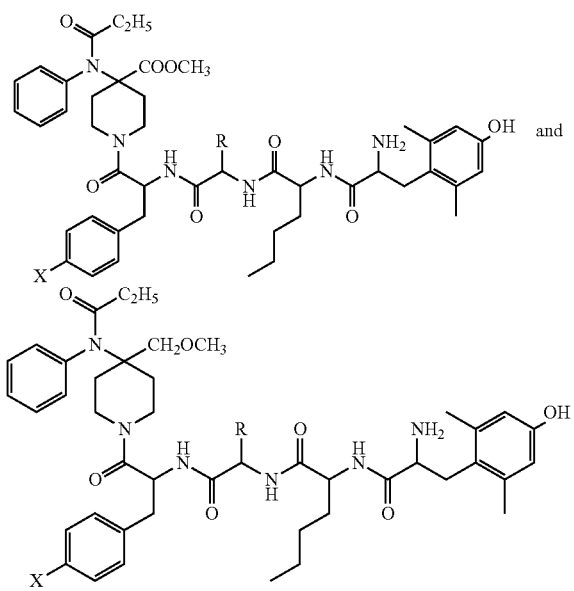

where X is H, Cl, F, alkyl, haloalkyl (e.g., —CF$_3$), etc.

Utility: Compounds of the invention can be used to modulate an opioid receptor in a subject. Such a method typically includes administering to a subject in need of an opioid receptor modulation a therapeutically effective amount of a compound of the invention. The compounds of the invention have a variety of physiological properties. In particular, the present inventors have discovered that some compounds of the invention can modulate a variety of receptors including, but not limited to, μ-opioid receptors, δ-opioid receptors or both. Accordingly, any clinical conditions that can be treated by activation or inhibition of one or more of these receptors can be treated by the compounds of the invention. In addition, some compounds of the invention are opioid antagonists. These compounds can be used to treat various addictions, as well as side-effects of opioid use.

In particular, some compounds of the invention can be used in a variety of clinical conditions associated with opioid use including, but not limited to, counteracting life-threatening depression of the central nervous and respiratory systems. Therefore, compounds of the invention can be used for emergency overdose and dependence treatment.

Compounds of the invention can modulate numerous central and peripheral effects including those associated with opioid abuse, the development of opioid tolerance and dependence, opioid-induced constipation, alcohol and cocaine abuse, depression, and immune responses. The diverse therapeutic applications of compounds of the invention include opioid-overdose-induced respiratory depression, opioid and cocaine abuse, alcohol dependence, smoking cessation, obesity, psychosis and for the treatment of dyskinesia associated with Parkinson's disease.

Compounds of the invention can also be used to treat various clinical conditions including, but not limited to, Raynaud's disease, hypertension, scleroderma, anxiety and panic disorders, and in the treatment of dyskinesia associated with Parkinson's disease.

Another aspect of the invention provides a method for modulating an opioid receptor in a subject, said method comprising administering to a subject in need of an opioid receptor modulation a therapeutically effective amount of a compound of Formula I. Generally, compounds of the invention are opioid receptor antagonists.

Still another aspect of the invention provides a method for treating pain, an opioid dependence or a clinical condition associated with an opioid overdose, said method comprising administering to a subject in need of such a treatment a therapeutically effective amount of a compound of Formula I. In some embodiments, the clinical condition associated with an opioid overdose comprises depression of the central nervous system, depression of respiratory system or a combination thereof.

Yet still another aspect of the invention provides a method for treating a clinical condition associated with opioid receptor activation, said method comprising administering to a subject in need of such a treatment a therapeutically effective amount of a compound of Formula I, wherein said clinical condition associated with opioid receptor activation is selected from the group consisting of: depression of the central nervous system due to opioid overdose; opioid-overdose-induced respiratory system depression; opioid abuse, addiction or development of tolerance and dependence, or a combination thereof; alcohol or cocaine abuse or addition; nicotine addiction; gambling addiction; depression; L-dopa-induced dyskinesia of Parkinson's disease; and opioid-induced gastrointestinal functional disorder.

Specific utilities for compounds of various opioid receptor antagonists are known. See, for example, Singleton et al., *Cancer*, 2015, 121(16), 2681-2688 (use of μ-opioid receptor antagonists in cancer treatment); Jackson et al., *Neuropharmacology*, 2015, 97, 270-274 (use of κ-opioid receptor antagonist for nicotine withdrawal); Bear et al., U.S. Pat. Appl. Publication No. US 20150202199 A1 (treatments for depression and other diseases using dopaminergic agents); Noble et al., *British Journal of Pharmacology*, 2015, 172 (16), 3964-3979 (opioid receptor antagonists for drug abuse and/or the prevention of relapse treatment); Brokjaer et al., *Neurogastroenterology & Motility*, 2015, 27(5), 693-704 (opioid antagonists for treatment of gastrointestinal side effects such as pain); Labuzek et al., *Pharmacological Reports*, 2014, 66(5), 811-820 (opioid antagonists for pharmacotherapy for gambling disorder); Soyka et al., *Current Drug Abuse Reviews*, 2008, 1(3), 280-291 (opioid antagonists for pharmacological treatment of alcohol dependence); Nutt et al., *Psychopharmacology*, (London, United Kingdom), 2014, 28(1), 8-22 (treatment of alcohol dependence); Tek et al., *Journal of Clinical Psychopharmacology*, 2014, 34(5), 608-612 (use of opioid antagonists in arresting antipsychotic-associated weight gain); Shi et al., *Guoji Yaoxue Yanjiu Zazhi*, 2013, 40(4), 439-442 (combinations of opioid agonists and opioid antagonists to treat side effects of opioid agonists and decrease risk of drug abuse); Wang et al., *Expert Opinion on Investigational Drugs*, 2013, 22(10), 1225-1227 (use of opioid antagonists for treatment of opioid-induced constipation); Taylor et al., *Expert Opinion on Investigational Drugs*, 2013, 22(4), 517-525 (use of opioid antagonists as analgesics); Zagon et al., PCT patent application publication number WO 2013016480 A1 (use of opioid antagonists for treatment of epithelial wounds); Pisak et al., PCT Patent Application Publication No. WO 2012/134410 A1 (use of opioid antagonists for treating scleroderma including systemic sclerosis); Hopp et al., PCT Patent Application Publication No. WO 2012089738 A1 (use of a combination of opioid agonists and opioid antagonists for the treatment of Parkinson's disease and associated symptoms); Tenhola et al., *J. Endocrinological Investigation*, 2012, 35(2), 227-230 (effect of opioid antagonists on sex hormone secretion, e.g., using an opioid antagonists to increase the secretion of GnRH in the hypothalamus which then causes a pulsatile release of LH in the pituitary and secretion of testosterone); Miller et al., *Amer. J. Health-System Pharmacy*, 2011, 68(15), 1419-1425 (use of opioid antagonists for management of opioid-induced pruritus); Toledano et al., U.S. Pat. Appl. Publ. No. 20110269727 A1 (using opioid antagonists and direct-acting $\alpha_2$-adrenergic agonists to reduce allodynic back pain); Pisak et al., PCT Patent Application Publication No. WO 2011123084 A1 (using an opioid receptor antagonist to treat herpes zoster disease); Ockert et al., *J. Addiction Med.*, 2011, 5(2), 110-114 (using an opioid antagonist for outpatient opioid detoxification and/or the treatment of opioid withdrawal); Moss et al., U.S. Pat. Appl. Publ. No. 20100286059 A1 (use of opioid antagonists for inhibiting or reducing, cellular proliferation and migration, such as endothelial cell proliferation and migration, including that associated with angiogenesis, as well as attenuating cancerous tumor growth and metastasis); Zagon et al., U.S. Pat. Appl. Publ. No. US 20100273821 A1 (using opioid antagonists to treat dry eye); Lobmaier et al., *Eur. J. Clin. Pharm.*, 2010, 66(6), 537-545 (use of the opioid antagonists for the treatment of intoxication and overdose); Stotts et al., *Expert Opinion on Pharmacotherapy*, 2009, 10(11), 1727-1740 (using opioid antagonists for treating opioid dependency); Hopp et al., PCT Patent Application Publication No. WO 2010003963 A1 (using opioid antagonists for treating urinary retention); and Hayward et al., PCT Patent Application Publication No. WO 2009156889 A1 (using opioid antagonists for treating obesity, obesity-related co-morbidities, and CNS disorders). Accordingly, compounds of the invention can be used treat all of these clinical conditions. In addition, compounds of the invention can be used in the treatment of various forms of depression and/or mood disorders, including, for example, breakthrough depression and treatment-refractory depression, and other mood disorders.

Some of the more specific exemplary clinical conditions that can be treated by compounds of the invention include, but are not limited to, hemorrhagic shock, nicotine withdrawal symptoms, gastrointestinal side effects of opioids, cancer therapy, epithelial wounds, herpes zoster infection, and opioid-induced pruritus.

One particular embodiment of the invention provides treating pain in a subject by administering to a subject in need of pain treatment a therapeutically effective amount of a compound of the invention. Without being bound by any theory, because compounds of the invention modulate both μ and δ-opioid receptors, there is a significantly less likelihood of developing addiction or abuse. That is, statistically one can expect at least 10% or more, typically at least 25% or more, often at least 50% or more, and more often at least 75% or more less likelihood of developing addiction and/or abuse using compounds of the invention compared to other conventional opioid ligands such as morphine.

Pharmaceutical Composition: The present invention includes pharmaceutical compositions comprising at least one compound of the invention or a pharmaceutically acceptable salt or solvate thereof, together with at least one pharmaceutically acceptable carrier, and optionally other therapeutic and/or prophylactic ingredients.

In general, the compounds of the invention are administered in a therapeutically effective amount by any of the accepted modes of administration for agents that serve similar utilities. Suitable dosage ranges are typically 1-500 mg daily, typically 1-100 mg daily, and often 1-30 mg daily, depending on numerous factors such as the severity of the disease to be treated, the age and relative health of the subject, the potency of the compound used, the route and form of administration, the indication towards which the administration is directed, and the preferences and experience of the medical practitioner involved. One of ordinary skill in the art of treating such diseases is typically able, without undue experimentation and in reliance upon personal knowledge and the disclosure of this application, to ascertain a therapeutically effective amount of the compounds of the invention.

Typically, compounds of the invention are administered as pharmaceutical formulations including those suitable for oral (including buccal and sub-lingual), rectal, nasal, topical, pulmonary, vaginal, or parenteral (including intramuscular, intraarterial, intrathecal, subcutaneous and intravenous) administration or in a form suitable for administration by inhalation or insufflation. Typical manner of administration is generally oral using a convenient daily dosage regimen which can be adjusted according to the degree of affliction.

A compound or compounds of the invention, together with one or more conventional adjuvants, carriers, or diluents, can be placed into the form of pharmaceutical compositions and unit dosages. The pharmaceutical compositions and unit dosage forms can be comprised of conventional ingredients in conventional proportions, with or without additional active compounds or principles, and the unit dosage forms can contain any suitable effective amount of the active ingredient commensurate with the intended daily dosage range to be employed. The pharmaceutical compositions can be employed as solids, such as tablets or filled capsules, semisolids, powders, sustained release formulations, or liquids such as solutions, suspensions, emulsions, elixirs, or filled capsules for oral use; or in the form of suppositories for rectal or vaginal administration; or in the form of sterile injectable solutions for parenteral use. Formulations containing about one (1) milligram of active ingredient or, more broadly, about 0.01 to about one hundred (100) milligrams, per tablet, are accordingly suitable representative unit dosage forms.

The compounds of the invention can be formulated in a wide variety of oral administration dosage forms. The pharmaceutical compositions and dosage forms can comprise a compound or compounds of the invention or pharmaceutically acceptable salts thereof as the active component. The pharmaceutically acceptable carriers can be either solid or liquid. Solid form preparations include powders, tablets, pills, capsules, cachets, suppositories, and dispersible granules. A solid carrier can be one or more substances which can also act as diluents, flavoring agents, solubilizers, lubricants, suspending agents, binders, preservatives, tablet disintegrating agents, or an encapsulating material. In powders, the carrier generally is a finely divided solid which is a mixture with the finely divided active component. In tablets, the active component generally is mixed with the carrier having the necessary binding capacity in suitable proportions and compacted in the shape and size desired. The powders and tablets preferably contain from about one (1) to about seventy (70) percent of the active compound. Suitable carriers include but are not limited to magnesium carbonate, magnesium stearate, talc, sugar, lactose, pectin, dextrin, starch, gelatine, tragacanth, methylcellulose, sodium carboxymethylcellulose, a low melting wax, cocoa butter, and the like. The term "preparation" is intended to include the formulation of the active compound with encapsulating material as carrier, providing a capsule in which the active component, with or without carriers, is surrounded by a carrier, which is in association with it. Similarly, cachets and lozenges are included. Tablets, powders, capsules, pills, cachets, and lozenges can be as solid forms suitable for oral administration.

Other forms suitable for oral administration include liquid form preparations including emulsions, syrups, elixirs, aqueous solutions, aqueous suspensions, or solid form preparations which are intended to be converted shortly before use to liquid form preparations. Emulsions can be prepared in solutions, for example, in aqueous propylene glycol solutions or may contain emulsifying agents, for example, such as lecithin, sorbitan monooleate, or acacia. Aqueous solutions can be prepared by dissolving the active component in water and adding suitable colorants, flavors, stabilizers, and thickening agents. Aqueous suspensions can be prepared by dispersing the finely divided active component in water with viscous material, such as natural or synthetic gums, resins, methylcellulose, sodium carboxymethylcellulose, and other well known suspending agents. Solid form preparations include solutions, suspensions, and emulsions, and can contain, in addition to the active component, colorants, flavors, stabilizers, buffers, artificial and natural sweeteners, dispersants, thickeners, solubilizing agents, and the like.

The compounds of the invention can also be formulated for parenteral administration (e.g., by injection, for example bolus injection or continuous infusion) and can be presented in unit dose form in ampoules, pre-filled syringes, small volume infusion or in multi-dose containers with an added preservative. The compositions can take such forms as suspensions, solutions, or emulsions in oily or aqueous vehicles, for example solutions in aqueous polyethylene glycol. Examples of oily or nonaqueous carriers, diluents, solvents or vehicles include propylene glycol, polyethylene glycol, vegetable oils (e.g., olive oil), and injectable organic esters (e.g., ethyl oleate), and can contain formulatory agents such as preserving, wetting, emulsifying or suspending, stabilizing and/or dispersing agents. Alternatively, the active ingredient can be in powder form, obtained by aseptic isolation of sterile solid or by lyophilization from solution for constitution before use with a suitable vehicle, e.g., sterile, pyrogen-free water.

The compounds of the invention can be formulated for topical administration to the epidermis as ointments, creams or lotions, or as a transdermal patch. Ointments and creams can, for example, be formulated with an aqueous or oily base with the addition of suitable thickening and/or gelling agents. Lotions can be formulated with an aqueous or oily base and will in general also contain one or more emulsifying agents, stabilizing agents, dispersing agents, suspending agents, thickening agents, or coloring agents. Formulations suitable for topical administration in the mouth include lozenges comprising active agents in a flavored base, usually sucrose and acacia or tragacanth; pastilles comprising the active ingredient in an inert base such as gelatine and glycerine or sucrose and acacia; and mouthwashes comprising the active ingredient in a suitable liquid carrier.

The compounds of the invention can be formulated for administration as suppositories. A low melting wax, such as a mixture of fatty acid glycerides or cocoa butter is first melted and the active component is dispersed homogeneously, for example, by stirring. The molten homogeneous mixture is then poured into convenient sized molds, allowed to cool, and to solidify.

The compounds of the invention can also be formulated for vaginal administration. Pessaries, tampons, creams, gels, pastes, foams or sprays containing in addition to the active ingredient such carriers as are known in the art to be appropriate.

The compounds of the invention can be formulated for nasal administration. The solutions or suspensions are applied directly to the nasal cavity by conventional means, for example, with a dropper, pipette or spray. The formulations can be provided in a single or multidose form. In the latter case of a dropper or pipette, this can be achieved by the patient administering an appropriate, predetermined volume of the solution or suspension. In the case of a spray, this can be achieved for example by means of a metering atomizing spray pump.

The compounds of the invention can be formulated for aerosol administration, particularly to the respiratory tract and including intranasal administration. The compound will generally have a small particle size for example of the order of five (5) microns or less. Such a particle size can be obtained by means known in the art, for example by micronization. The active ingredient is provided in a pressurized pack with a suitable propellant such as a chlorofluorocarbon (CFC), for example, dichlorodifluoromethane, trichlorofluoromethane, or dichlorotetrafluoroethane, or carbon dioxide or other suitable gas. The aerosol can conveniently also contain a surfactant such as lecithin. The dose of drug can be controlled by a metered valve. Alternatively the active ingredients can be provided in a form of a dry powder, for example, a powder mix of the compound in a suitable powder base such as lactose, starch, starch derivatives such as hydroxypropylmethyl cellulose and polyvinylpyrrolidine (PVP). The powder carrier typically forms a gel in the nasal cavity. The powder composition can be presented in unit dose form, for example, in capsules or cartridges of e.g., gelatine or blister packs from which the powder can be administered by means of an inhaler.

When desired, formulations can be prepared with enteric coatings adapted for sustained or controlled release administration of the active ingredient. For example, the compounds of the invention can be formulated in transdermal or subcutaneous drug delivery devices. These delivery systems are advantageous when sustained release of the compound is necessary or desired and when patient compliance with a treatment regimen is crucial. Compounds in transdermal delivery systems are frequently attached to a skin-adhesive solid support. The compound of interest can also be combined with a penetration enhancer, e.g., Azone (1-dodecylazacycloheptan-2-one). Sustained release delivery systems can be inserted subcutaneously into the subdermal layer by surgery or injection. The subdermal implants encapsulate the compound in a lipid soluble membrane, e.g., silicone rubber, or a biodegradable polymer, e.g., polylactic acid.

The pharmaceutical preparations are typically in unit dosage forms. In such form, the preparation is often subdivided into unit doses containing appropriate quantities of the active component. The unit dosage form can be a packaged preparation, the package containing discrete quantities of preparation, such as packeted tablets, capsules, and powders in vials or ampoules. Also, the unit dosage form can be a capsule, tablet, cachet, or lozenge itself, or it can be the appropriate number of any of these in packaged form.

Other suitable pharmaceutical carriers and their formulations are described in Remington: *The Science and Practice of Pharmacy* 1995, edited by E. W. Martin, Mack Publishing Company, 19th edition, Easton, Pa.

When it is possible that, for use in therapy, therapeutically effective amounts of a compound of Formula I, as well as pharmaceutically acceptable salts thereof, can be administered as the raw chemical, it is possible to present the active ingredient as a pharmaceutical composition. Accordingly, the disclosure further provides pharmaceutical compositions, which include therapeutically effective mounts of compounds of Formula I or pharmaceutically acceptable salts thereof or a prodrug thereof, and one or more pharmaceutically acceptable carriers, diluents, or excipients. When applied to a combination, the term refers to combined amounts of the active ingredients that result in the therapeutic effect, whether administered in combination, serially, or simultaneously. The compounds of Formula I and pharmaceutically acceptable salts thereof, are as described above. The carrier(s), diluent(s), or excipient(s) must be acceptable in the sense of being compatible with the other ingredients of the formulation and not deleterious to the recipient thereof. In accordance with another aspect of the disclosure there is also provided a process for the preparation of a pharmaceutical formulation including admixing a compound of Formula I, or a pharmaceutically acceptable salt thereof or a prodrug thereof, with one or more pharmaceutically acceptable carriers, diluents, or excipients.

When the compositions of this disclosure comprise a combination of a compound of the present disclosure and one or more additional therapeutic or prophylactic agent, both the compound and the additional agent are usually present at dosage levels of between about 10 to 150%, and more typically between about 10 and 80% of the dosage normally administered in a monotherapy regimen.

Additional objects, advantages, and novel features of this invention will become apparent to those skilled in the art upon examination of the following examples thereof, which are not intended to be limiting. In the Examples, procedures that are constructively reduced to practice are described in the present tense, and procedures that have been carried out in the laboratory are set forth in the past tense.

EXAMPLES

Compounds of the invention are synthesized using the procedures described in Petrov et al., *Bioorganic & Medicinal Chemistry Letters*, 2006, 16(18), 4946-4950 and Petrov et al., *Bioorganic & Medicinal Chemistry Letters*, 2013, 23(11), 3434-3437.

Compounds of the invention are synthesized using the general reaction Scheme I outlined below and using the various procedures described in Bagley et al., in "New 4-(heteroanilido)piperidines, structurally related to the pure opioidagonist fentanyl, with agonist and/or antagonist properties," *J. Med. Chem.*, 1989, 32(3), 663-671; France et al., in "Pharmacological profile of a novel fentanyl derivative with opioid and nonopioid effects," *J. Pharm. and Exp. Therap.*, 1991, 258(2), 502-510; Egan et al., in "Mirfentanil and A-4334. Tritiation at high specific activity," *Applied Radiation and Isotopes*, 2009, Volume Date 2010, 68(1), 120-121; Aceto et al., M. D.; Bowman, E. R.; Harris, L. S.; Hughes, Larry D.; Kipps et al., in "Dependence studies of new compounds in the rhesus monkey, rat and mouse (2002)," From NIDA Research Monograph (2003), 183 (Problems of Drug Dependence 2002), 191-227; and Gerak et al. in "Effects of a Novel Fentanyl Derivative on Drug Discrimination and Learning in Rhesus Monkeys," *Pharmacology, Biochemistry and Behavior*, 1999, 64(2), 367-371, all of which are incorporated herein by reference in their entirety.

SCHEME I

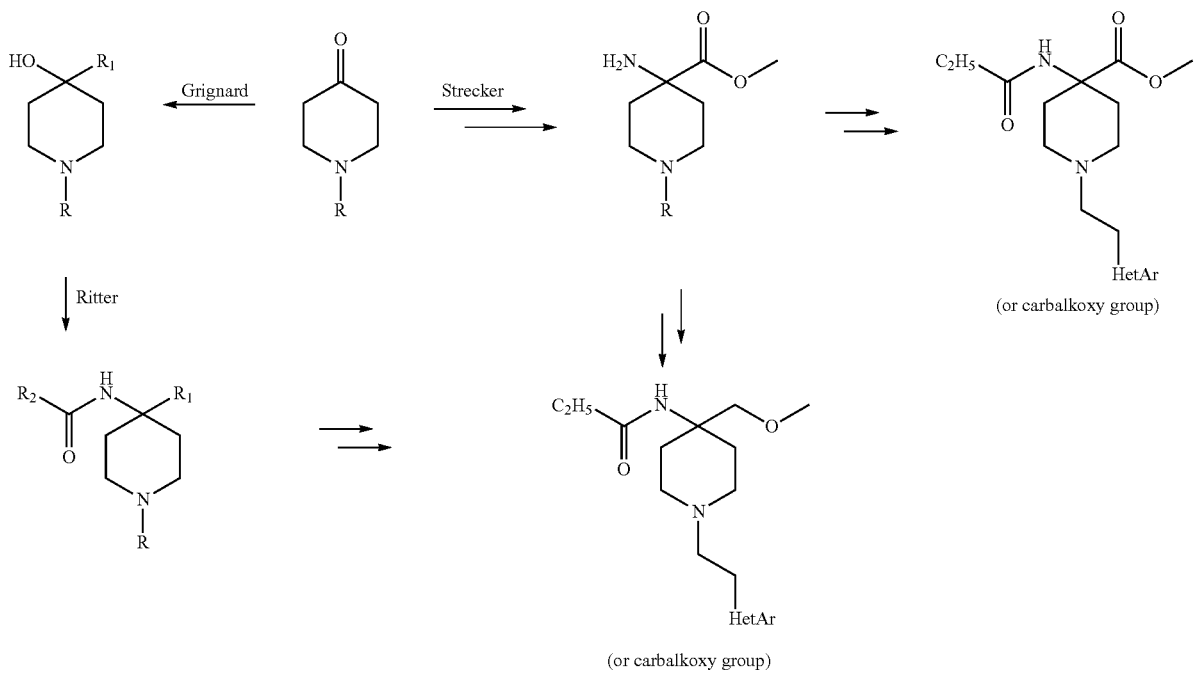

The foregoing discussion of the invention has been presented for purposes of illustration and description. The foregoing is not intended to limit the invention to the form or forms disclosed herein. Although the description of the invention has included description of one or more embodiments and certain variations and modifications, other variations and modifications are within the scope of the invention, e.g., as may be within the skill and knowledge of those in the art, after understanding the present disclosure. It is intended to obtain rights which include alternative embodiments to the extent permitted, including alternate, interchangeable and/or equivalent structures, functions, ranges or steps to those claimed, whether or not such alternate, interchangeable and/or equivalent structures, functions, ranges or steps are disclosed herein, and without intending to publicly dedicate any patentable subject matter. All references cited herein are incorporated by reference in their entirety.

What is claimed is:
1. A compound of the formula:

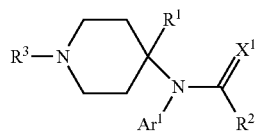

I wherein
Ar$^1$ is H or optionally substituted heteroaryl;
R$^1$ is a heteroalkyl;
R$^2$ is alkyl;
R$^3$ is an oligopeptide;
R$^4$ is alkylene;
each of X$^1$ is O, NR$^6$ or S; and
each of R$^5$ and R$^6$ is independently H or alkyl.

2. The compound of claim 1, wherein Ar$^1$ is optionally substituted pyridyl or optionally substituted pyrazyl.
3. The compound of claim 1, wherein R$^1$ is a heteroalkyl of the formula:

—C(=O)—OR$^7$ or —R$^8$—X$^4$—R$^9$ wherein
each of R$^7$ and R$^9$ is independently H or alkyl;
R$^8$ is alkylene;
X$^4$ is O, NR$^{10}$ or S; and
R$^{10}$ is H, alkyl or a nitrogen protecting group.
4. The compound of claim 3, wherein R$^1$ is a heteroalkyl of the formula: —C(=O)—OR$^7$, wherein R$^7$ is as defined in claim 3.
5. The compound of claim 4, wherein R$^7$ is alkyl.
6. The compound of claim 3, wherein R$^1$ is a heteroalkyl of the formula: —R$^8$—X$^4$—R$^9$, wherein R$^8$, X$^4$ and R$^9$ are as defined in claim 3.
7. The compound of claim 6, wherein R$^8$ is methylene.
8. The compound of claim 6, wherein X$^4$ is O.
9. The compound of claim 6, wherein R$^9$ is alkyl.
10. The compound of claim 1, wherein R$^3$ is an oligopeptide having 3 or 4 amino acid residues.
11. The compound of claim 10, wherein said oligopeptide is a moiety of the formula:

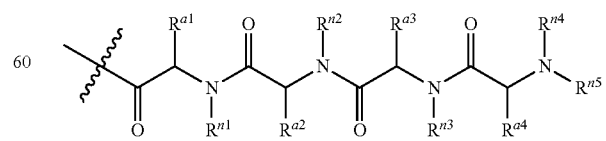

wherein
each of R$^{a1}$, R$^{a2}$, R$^{a3}$ and R$^{a4}$ is independently amino acid side-chain; and each of $R^{n1}$, $R^{n2}$, $R^{n3}$, $R^{n4}$ and $R^{n5}$ is independently H, alkyl or a nitrogen protecting group.

12. The compound of claim 10, wherein said oligopeptide is a moiety of the formula:

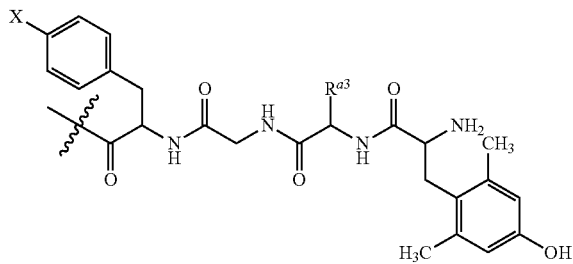

wherein
X is halide; and
$R^{a3}$ is alkyl.

13. The compound of claim 1, wherein said compound is a selective μ-opioid receptor agonist, a selective δ-opioid receptor agonist, or a combination thereof.

14. The compound of claim 1, wherein said compound is an opioid receptor antagonist.

15. A method for treating pain, an opioid dependence or a clinical condition associated with an opioid overdose, said method comprising administering to a subject in need of such a treatment a therapeutically effective amount of a compound of claim 1.

16. The method of claim 15, wherein said clinical condition associated with an opioid overdose comprises depression of the central nervous system, depression of respiratory system or a combination thereof.

17. A method for treating a clinical condition associated with opioid receptor activation, said method comprising administering to a subject in need of such a treatment a therapeutically effective amount of a compound of claim 1, wherein said clinical condition associated with opioid receptor activation is selected from the group consisting of: depression of the central nervous system due to opioid overdose; opioid-overdose-induced respiratory system depression; opioid abuse, addiction or development of tolerance and dependence, or a combination thereof; alcohol or cocaine abuse or addition; nicotine addiction; gambling addiction; depression; L-dopa-induced dyskinesia of Parkinson's disease; and opioid-induced gastrointestinal functional disorder.

18. The method of claim 15, wherein said oligopeptide is a moiety of the formula:

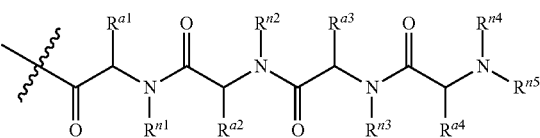

wherein
each of $R^{a1}$, $R^{a2}$, $R^{a3}$ and $R^{a4}$ is independently amino acid side-chain; and
each of $R^{n1}$, $R^{n2}$, $R^{n3}$, $R^{n4}$ and $R^{n5}$ is independently H, alkyl or a nitrogen protecting group.

19. A compound of the formula:

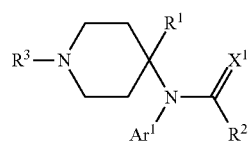

I wherein
$Ar^1$ is optionally substituted pyridyl or optionally substituted pyrazyl;
$R^1$ is a heteroalkyl;
$R^2$ is alkyl;
$R^3$ is an oligopeptide or a moiety of the formula —$R^4$—Y;
$R^4$ is alkylene;
Y is optionally substituted heteroaryl, or optionally substituted aryl;
each of $X^1$ is O, $NR^6$ or S; and
each of $R^5$ and $R^6$ is independently H or alkyl.

20. The compound of claim 19, wherein $R^1$ is a heteroalkyl of the formula:

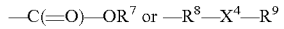

wherein
each of $R^7$ and $R^9$ is independently H or alkyl;
$R^8$ is alkylene;
$X^4$ is O, $NR^{10}$ or S; and
$R^{10}$ is H, alkyl or a nitrogen protecting group.

* * * * *